United States Patent [19]

Sheiham et al.

[11] Patent Number: 5,364,830
[45] Date of Patent: Nov. 15, 1994

[54] RECORD MATERIAL USING VINYL CARBINOL COLOR FORMERS

[75] Inventors: Ivan Sheiham, Marlow; Margaret P. Templey, Thame, both of United Kingdom

[73] Assignee: The Wiggins Teape Group Limited, London, England

[21] Appl. No.: 34,461

[22] Filed: Mar. 19, 1993

[30] Foreign Application Priority Data

Mar. 20, 1992 [GB] United Kingdom ............... 9206132

[51] Int. Cl.$^5$ .................. B41M 5/20; C07D 295/00; C07D 401/00; C07C 211/00
[52] U.S. Cl. .................................. 503/224; 503/223; 544/106; 544/129; 546/192; 546/208; 564/433; 548/523; 548/577
[58] Field of Search ............... 564/433; 503/224, 223; 427/150, 151; 546/192, 208, 184, 187, 578, 563; 544/106, 129

[56] References Cited

U.S. PATENT DOCUMENTS

| | | | |
|---|---|---|---|
| 3,930,108 | 12/1975 | Alsop | 428/411 |
| 3,957,288 | 5/1976 | Lemahieu et al. | 282/27.5 |
| 4,355,823 | 10/1982 | Barri | 503/223 |
| 4,808,566 | 2/1989 | Takashima et al. | 503/223 |
| 4,939,117 | 7/1990 | Kusakata et al. | 503/224 |
| 5,190,909 | 3/1993 | Shanton et al. | 503/218 |

FOREIGN PATENT DOCUMENTS

| | | |
|---|---|---|
| 0154528 | 9/1985 | European Pat. Off. . |
| 0315901 | 5/1989 | European Pat. Off. . |
| 0429239 | 5/1991 | European Pat. Off. . |
| 0433024 | 6/1991 | European Pat. Off. . |
| 2212788 | 7/1974 | France . |
| 2294055 | 7/1976 | France . |
| 2362956 | 7/1974 | Germany . |
| 04108864 | 4/1992 | Japan . |
| 04112077 | 4/1992 | Japan . |
| 04117350 | 4/1992 | Japan . |
| 04151285 | 5/1992 | Japan . |
| 04182186 | 6/1992 | Japan . |
| 04185482 | 7/1992 | Japan . |
| 870476 | 6/1961 | United Kingdom . |
| 1432505 | 4/1976 | United Kingdom . |
| 1456208 | 11/1976 | United Kingdom . |
| 1465669 | 2/1977 | United Kingdom . |

OTHER PUBLICATIONS

Akiyama et al., "Diphenylmethane and Triphenylmethane Dye Ethynovinylogues with Absorption Bands in the Near-Infrared", 9 *Dyes and Pigments* 459–66 (1988).

Gautier et al., "Condensation du Dimsylsodium Avec les Cetones α-Ethyleniques", *Tetrahedron Letters No. 12*, 895–98 (1970).

Gilman et al., "Addition Reactions of Organometallic Compounds with Conjugated Systems", 63 *Journal of the American Chemical Society* 2046–48 (Aug. 1941).

Lutz et al., "The Effect of Configuration on the Reactivity of the Chalcone System", 77 *Journal of the American Chemical Society* 1814–18 (Apr. 1955).

Miocque et al., "Synthese et étude pharmacologique de dérivés du naphtyl-2 méethylsulfoxyde", *Chimie Therapeutique*, 1972, Jul.-Aug., No. 4.

Primary Examiner—Richard L. Raymond
Assistant Examiner—Deborah Lambkin
Attorney, Agent, or Firm—Burns, Doane, Swecker & Mathis

[57] ABSTRACT

Pressure or heat sensitive record materials with color-former sublimation problems reduced or eliminated whilst not reducing the color forming capability per unit weight of color former by providing what are in effect dimers of vinyl carbinols, with the vinyl carbinol residues, linked through the aryl groups of a diaryl amine.

10 Claims, 2 Drawing Sheets

RECORD MATERIAL USING VINYL CARBINOL COLOR FORMERS

This invention relates to record material utilising a vinyl carbinol or a derivative thereof as a chromogenic compound. The record material may be pressure sensitive or heat sensitive, and in either case, image formation occurs by a reaction between the chromogenic material and a suitable colour developer to produce a coloured species.

As is well known in the art, pressure sensitive record material typically functions by separating the colour reactive components by a pressure rupturable barrier. Most commonly this barrier is provided by micro-encapsulating a solution, in a suitable organic solvent, of one of the reactive components. On application of imaging pressure the microcapsules are ruptured, liberating the solution of one of the reactive components into reactive contact with the other component and forming a coloured mark or image corresponding to the applied imaging pressure. It is also known to use other forms of pressure rupturable barrier such as a dispersion of a solution in a waxy continuous layer or a honeycomb structure instead of microcapsules.

Pressure sensitive record material can be of two basic types, "transfer" and "self contained". In the transfer type the reactive components are present in coatings on facing surfaces of upper and lower sheets, the coating on the lower surface of the upper sheet comprising an isolated, usually micro-encapsulated, solution of one reactive component and the coating on the upper surface of the lower sheet comprising the other component. Most commonly it is the chromogenic material which is present in the coating of the upper sheet, the colour developer, such as a clay or resin, being present in the coating of the lower sheet. This is the "normal transfer" system. An alternative is the "reverse transfer" system in which a colour developer is dissolved and micro-encapsulated or otherwise isolated in the coating of the upper sheet and the chromogenic material is present, usually adsorbed on a suitable particulate carrier, in the coating of the lower sheet.

In transfer pressure sensitive record material sheets carrying micro-encapsulated or otherwise isolated chromogenic material on their lower surfaces are usually referred to as "CB" (coated back) sheets and sheets carrying a colour developer coating on their upper surfaces are usually referred to as "CF" (coated front) sheets, and the terminology is used similarly for other coatings. In addition it is common to use intermediate sheets which carry appropriate coatings on both upper and lower surfaces and these are usually referred to as "CFB" (coated front and back) sheets.

In self contained pressure sensitive sheet record material, both reactive components are present on or in a single sheet. Premature reaction is inhibited by microencapsulating one of the components, usually the chromogenic material. The reactive components can be present in one or more coatings on the sheet surface ("coated" self contained) or dispersed within the body of the sheet ("loaded" self contained).

In heat sensitive sheet record material, the reactive components, i.e. the chromogenic material and the colour developer are initially present in a mutually unreactive state and are enabled to react together by changes brought about by heat. Most commonly this is achieved by including the chromogenic material and colour developer as solids. On heating, the chromogenic material and/or the colour developer and/or another component of the system is melted and thus permits reactive contact between the chromogenic material and colour developer. Alternatively, the chromogenic material and the colour developer may be micro-encapsulated or otherwise isolated in solution as for pressure sensitive record material. Imaging then occurs on heat induced rupture or increased wall permeability of the isolating system. Numerous chromogenic compounds have been used or proposed for use in record material as described above. In particular in The Wiggins Teape Group Limited's EP-A-0,429,239 there are disclosed pressure or heat sensitive record materials utilising chromogenic materials from such formulae as:

or corresponding isomeric compounds:

While the above materials have proved to be good colour formers, certain of them show problems in some circumstances. In particular, certain of the materials are subject to sublimation, with consequent potential development of undesired overall coloration.

The present invention achieves elimination or reduction of sublimation problems, whilst not reducing the colour forming capability per unit weight of colour former in spite of the large molecule, by providing what are in effect dimers of the EP-A-0,429,239 compounds, believed to be new both in themselves and in their use as colour formers in pressure or heat sensitive record material.

The new compounds are of structure or structural isomers thereof in which one or both of the ethylenic links are adjacent to the terminal rather than the central aryl groups, i.e. compounds of the structure (IIIb)

(IIIc)

(IIId)

wherein

A₁ and A₂ are independently hydrogen or aryl particularly phenyl

R¹ is hydrogen, alkyl particularly C₁–C₈ alkyl, or aralkyl particularly benzyl

R² to R⁵ are independently hydrogen, halogen, particularly chloro or bromo, alkyl particularly C₁–C₈alkyl, alkoxy particularly C₁–C₈ alkoxy, or aralkoxy particularly benzyloxy, with the additional possibilities for R² and R³ of primary or secondary amino and N-heterocyclic, particularly dimethylamino or other di(C₁–C₈) alkylamino, dibenzylamino, piperidino, pyrrolidino and morpholino R⁶ and R⁷ are independently hydrogen, alkyl particularly C₁–C₈ alkyl, aryl particularly phenyl, or aralkyl particularly benzyl.

Synthesis of these compounds is described below, or the "a" form may be converted into the "b" form as disclosed in synthesis example 6 of EP-A-0,429,239.

Specific examples of sub-classes of compounds of formula (III) are those in which:

R₁ is methyl, n-butyl, n-octyl, or benzyl.

R₂, R₃ are independently hydrogen, methyl, bromo, methoxy, n-butoxy, n-octyloxy, benzyloxy, dimethylamino, dibenzylamino, piperidino, pyrrolidino or morpholino.

R₄, R₅ are independently hydrogen, chloro, methyl, methoxy, n-butoxy, n-octyloxy or benzyloxy; and R₆, R₇ are independently hydrogen, methyl, ethyl or iso-propyl.

Of particular interest within formula (III) are (XIV) given below in Example 1, and Compounds 1 to 27 of Table 1 below, all of form A-B-A and including the compounds of Examples 2 to 8. Summarised product data are given (except for compounds 8, 15, 24 and 25 not so far synthesized), first for the chalcone (yield g and % theory, and m.p. °C.) then for the carbinol or ether form (yield as for chalcone, and solution adsorption λ max nm). Examples illustrate particular syntheses, but other compounds synthesized were made in closely comparable ways.

TABLE 1

| A | B |
|---|---|
| 1. (Example 4) | |
|  |  |
| (For data see the example) | |
| 2. (Example 3) | |
|  |  |
| (For data see the example) | |
| 3. (Example 2) | |

TABLE 1-continued

| A | B |
|---|---|
| CH₃O—⌬—CH(O-i-C₃H₇)—CH=CH— | N(CH₂—⌬)(—⌬—)(—⌬—) |

(For data see the example)

4. (Example 5)

| | |
|---|---|
| C₄H₉O—⌬—CH(O-i-C₃H₇)—CH=CH— | —⌬—N(CH₃)—⌬— |

(For data see the example)

5.

| | |
|---|---|
| C₈H₁₇O—⌬—CH(O-i-C₃H₇)—CH=CH— | —⌬—N(CH₃)—⌬— |

| Data | 16.3 g (93.0%) | 149.7~151.4 | 8.6 g (quantitative) | 576 |
|---|---|---|---|---|

6. (Example 6)

| | |
|---|---|
| C₆H₅CH₂O—⌬—CH(OCH(CH₃)C₃H₇)—CH=CH— | —⌬—N(CH₃)—⌬— |

(For data see the example)

7.

| | |
|---|---|
| 3,4-(CH₃O)₂—⌬—CH(O-i-C₃H₇)—CH=CH— | —⌬—N(CH₃)—⌬— |

| Data | 13.2 g (93.7%) | 120.0~129.0 | 7.4 g (quantitative) | 636 |
|---|---|---|---|---|

8.

| | |
|---|---|
| C₂H₅O—⌬—CH(O-i-C₃H₇)—CH=CH— | —⌬—N(CH₃)—⌬— |

(Data not to hand)

9.

| | |
|---|---|
| (CH₃)₂N—⌬—CH(O-i-C₃H₇)—CH=CH— | —⌬—N(CH₃)—⌬— |

| Data | 6.9 g (52.1%) | 207.2~211.5 | 6.3 g (quantitative) | 700 |
|---|---|---|---|---|

10.

TABLE 1-continued

| A | | B | |
|---|---|---|---|
| (CH₃)₂N–C₆H₄–CH(O-i-C₃H₇)–CH=CH– | | 4-CH₃-C₆H₄–N(C₄H₉)–C₆H₄-4– | |
| Data 11. | 6.1 g (42.7%) 136.5~138.4 | 1.5 g (22.0%) | 705 |
| (CH₃)₂N–C₆H₄–CH(O-i-C₃H₇)–CH=CH– | | 4-CH₃-C₆H₄–N(C₈H₁₇)–C₆H₄-4– | |
| Data 12. | 9.0 g (57.4%) 191.0~193.0 | 5.5 g (76.9%) | 703 |
| (CH₃)₂N–C₆H₄–CH(O-i-C₃H₇)–CH=CH– | | 4-CH₃-C₆H₄–N(CH₂C₆H₅)–C₆H₄-4– | |
| Data 13. | 11.5 g (76.0%) 180.0~197.0 | 6.0 g (quantitative) | 698 |
| (C₄H₉)₂N–C₆H₄–CH(O-i-C₃H₇)–CH=CH– | | 4-CH₃-C₆H₄–N(CH₃)–C₆H₄-4– | |
| Data 14. | 3.4 g (48.0%) 172.4~174.1 | 1.2 g (59.0%) | 687 |
| [C₆H₅CH₂]₂N–C₆H₄–CH(OCH(CH₃)C₃H₇)–CH=CH– | | 4-CH₃-C₆H₄–N(CH₃)–C₆H₄-4– | |
| Data 15. | 10.6 g (60.0%) amorphous | 4.5 g (quantitative) | 704 |
| (C₂H₅)₂N–(3-Cl-C₆H₃)–CH(O-i-C₃H₇)–CH=CH– | | 4-CH₃-C₆H₄–N(CH₃)–C₆H₄-4– | |
| 16. | (Data not to hand) | | |
| pyrrolidino–C₆H₄–CH(O-i-C₃H₇)–CH=CH– | | 4-CH₃-C₆H₄–N(CH₃)–C₆H₄-4– | |
| Data 17. | 13.5 g (92.9%) 225~270 | 6.4 g (95.0%) | 705 |

TABLE 1-continued

| A | B |
|---|---|
| Ph–CH(O-i-C$_3$H$_7$)–CH=CH– | 4-(N(CH$_3$)(4-tolyl))phenyl– |
| Data 18. 5.5 g (50.0%) amorphous | 5.1 g (96.0%) 517 |
| Ph–CH(O-i-C$_3$H$_7$)–CH=CH– | 4-(N(C$_4$H$_9$)(4-tolyl))phenyl– |
| Data 19. 11.5 g (94.5%) 73.9~79.7 | 4.4 g (76.0%) 515 |
| Ph–CH(O-i-C$_3$H$_7$)–CH=CH– | 4-(N(C$_8$H$_{17}$)(4-tolyl))phenyl– |
| Data 20. 7.2 g (26.6%) 108~111 | 4.2 g (quantitative) 525 |
| Ph–CH(O-i-C$_3$H$_7$)–CH=CH– | 4-(N(CH$_2$Ph)(4-tolyl))phenyl– |
| Data 21. 20.1 g (86.1%) 106~114 | 6.4 g (quantitative) 530 |
| 4-CH$_3$-C$_6$H$_4$–CH(O-i-C$_3$H$_7$)–CH=CH– | 4-(N(CH$_3$)(4-tolyl))phenyl– |
| Data 22. 10.9 g (92.2%) 182.0~185.0 | 5.5 g (99.1%) 537 |
| 4-Br-C$_6$H$_4$–CH(O-i-C$_3$H$_7$)–CH=CH | 4-(N(CH$_3$)(4-tolyl))phenyl– |
| Data 23. (Example 7) 13.8 g (91.8%) amorphous | 6.2 g (90.1%) 520 |
| 4-CH$_3$O-C$_6$H$_4$–CH(OH)–CH=CH– | 4-(N(CH$_3$)(4-tolyl))phenyl– |

Made from the chalcone of Example 1 in 98.6% yield (2.5 g) λmax 575 nm, by sodium borohydride reduction.

24.

| 4-CH$_3$O-C$_6$H$_4$–CH(O–CH$_3$)–CH=CH– | 4-(N(CH$_3$)(4-tolyl))phenyl– |

TABLE 1-continued

| A | B |
|---|---|
| (Data not to hand) 25.  |  |
| (Data not to hand) 26.  |  |
| Data 15.6 g (quantitative) 108–126 | 6.0 g (89.5%) 500 |
| 27. (Example 8)  |  |
| (For data see the example) | |

In general, compounds in which $R^2$ and $R^3$ are hydrogen give magenta colours, compounds in which $R^2$ and $R^3$ are primary or secondary amino or N-heterocyclic give green colours, and compounds in which $R^2$ and $R^3$ are alkoxy or benzyloxy give blue colours. In each case however the precise hue will depend on the particular substituents present and the nature of $R^1$ and $R^4$ to $R^7$.

In outline the compounds of the invention may be prepared for example by condensation of a ketone such as p-methoxy acetophenone:

(IVa)

with a difunctional aldehyde:

(IVb)

to give:

(V)

which by reaction with phenyl lithium or the like is converted to:

(VI)

or which by suitable reduction techniques is converted to:

where $R^6$ and $R^7$ are hydrogen or alkyl depending on the reduction technique used. For example, reduction with an alkali metal borohydride such as sodium borohydride gives a product in which $R^6$ and $R^7$ in formula (VII) are hydrogen. Alternatively, reduction by the Meerwein-Ponndorf-Verley reduction ("MPV reduction") gives compounds in which $R^6$ and $R^7$ are isopropyl. The MPV reduction involves reaction of compound (V) with tri-isopropoxy aluminium in a secondary alcohol, for example, isoamyl alcohol or isopropyl alcohol and is described for example in "Advanced Organic Chemistry-Reactions, Mechanisms and Structure" by Jerry March, Second Edition, 1977, McGraw Hill International Book Company.

In preparing the compounds of formula (VI) the initial lithium-containing reaction product is washed to remove the lithium.

The alternative of condensation of aldehydes with difunctional ketones is illustrated for example in:

which affords an instance of compounds with $R^1$=hydrogen and when for example reacted with where $R^1$, $R^6$ and $R^7$ are as in formula (III) and each $R^8$ is independently hydrogen, alkyl particularly $C_1$-$C_8$ alkyl, aryl particularly phenyl, aralkyl particularly benzyl, or the two $R^8$ groups and the nitrogen atom to which they are attached together form a heterocyclic ring, —N($R^8$)$_2$ being an example of the substituted amino group possibility for $R^2$ and $R^3$ in formula (III).

Such diketones may for example be made by such a reaction as:

and then with tri-isopropyl aluminium affords initially the compound corresponding to (V) above and then that corresponding to (VII) above, but with the double bonds adjacent to the outer rather than the central benzene rings ($R^6$=$R^7$=i−Pr).

The compounds illustrated above are symmetrical but other possibilites are evident from reaction of the difunctional aldehyde or ketone starting material with successive equivalents of different ketones or aldehydes as the case may be, separating the mixed products if desired, or from reaction of difunctional starting materials having a ketone group at one end and an aldehyde group at the other, successively with the two corresponding monofunctional starting materials. The last-mentioned reaction sequence produces compounds of the structure (IIIc) or (IIId) referred to above.

The following examples illustrate the invention.

EXAMPLE 1

4,4′-Bis[3-(4-methoxyphenyl)-3-iso-propoxy-1-propenyl]-N-methyldiphenyl amine

The following synthesis was carried out:

STAGE 1

4,4′-Bis[3-(4-methoxyphenyl)-3-oxo-1-propenyl]-N-methyldiphenylamine

4-Methoxyacetophenone (18.0 g, 0.12 mol) and 4,4′-diformyl-N-methyldiphenyl amine (12.0 g, 0.05 mol) were dispersed in ethanol (150 ml) -in a 300 ml three-necked round bottom flask fitted with a mechanical stirrer and a water cooled condenser.

The third neck was stoppered and used to obtain samples for monitoring during the reaction.

Aqueous sodium hydroxide solution (20 ml of 30 w/v%) was added dropwise to the vigorously stirred ethanolic suspension at ambient temperature. A yellowish orange solid started separating from the reaction mixture immediately. Stirring was continued for about twenty four hours and the title compound was isolated by vacuum filtration, washed successively with water and dried. 24.3 g of the crude solid was purified with methanol and dried to give 21.0 g (83.5% of theory) of 4,4′-Bis[3-(4-methoxyphenyl)-3-oxo-1-propenyl]-N-methyl-diphenylamine with a melting point of 119.5°~193.0° C.

STAGE 2

4,4′-Bis[3-(4-methoxyphenyl)-3-iso-propoxy-1-propenyl]-N-methyldiphenyl amine 4,4′-Bis[3-(4-methoxyphenyl)-3-oxo-1-propenyl]-N-methyl-diphenylamine (10.1 g, 0.02 mol) prepared in Stage 1 above and aluminium-iso-propoxide (16.3 g, 0.08 mol) were dispersed in iso-amylalcohol (100 ml).

The temperature of reaction mixture was raised to 110° C. and the reaction was continued for two and a quarter hours distilling out iso-amylalcohol gradually. After the reaction was complete, the reaction mixture was poured into ice water (500 cc) and extracted with toluene (200 cc). The toluene layer was treated with active carbon and evaporated under reduced pressure to give 10.0 g of the title compound in a "tar" state.

Figure 1:
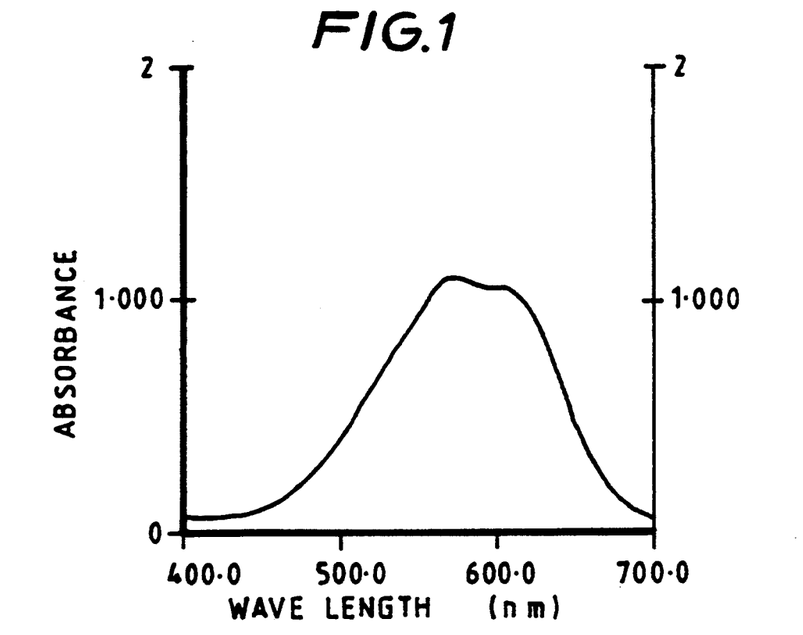
FIG. 1 absorbtion (solution) spectra of the compound of Example 1.

Spectra were then taken as follows:

1. Absorbtion (Solution) Spectrum 200 mg of the product XIV was dissolved and diluted to 50 ml with acetone. 5 ml of the above solution was taken and diluted to 100 ml with ethylacetate. Then 5 ml of the above solution was taken and diluted to 100 ml with 5 ml of 0.5% (w/v) $SnCl_4$-ethylacetate solution and ethylacetate. The absorption spectrum of the solution was measured with a spectrophotometer (Shimadzu UV 250). FIG. 1 plots absorbance against wavelength, λ max was 570 nm.

Figure 2A:
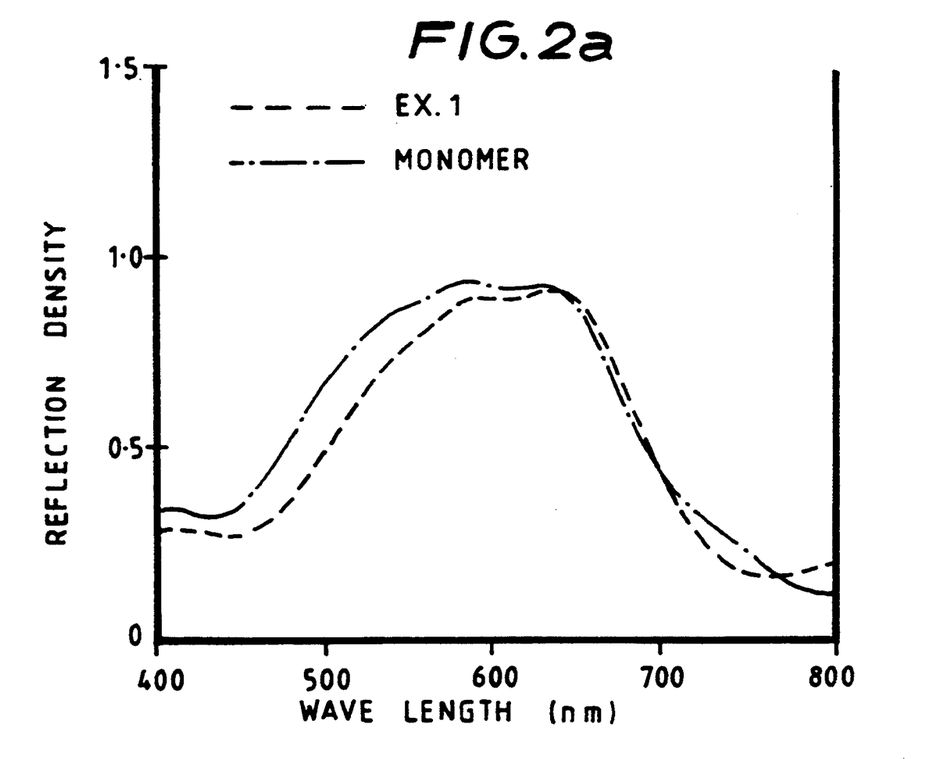
FIG. 2a reflection density spectra of the compound of Example 1 on clay CF from an "open" system coating, with the corresponding spectra of the "monomer" (compound I earlier herein)

2. Reflectance Spectrum 12 g of a 12% (w/w) solution of gelatin-gum arabic (1:1), 0.6 ml of a 7%(w/w) solution of XIV in a commercially available pressure sensitive record material solvent ("KMC-11-3" diisopropyl naphthalene isomer blend) and a small amount of defoaming agent were mixed, homogenized at 15,000 rpm for five minutes at 60° C. and kept until the foam disappeared. Then 3 ml emulsion was hand coated onto neutral-sized paper to give a CB sheet of the so-called "continuous" or "open phase" type; it was dried at ambient temperature, and calendered against inorganic clay CF paper, acid-washed montmorillonite giving a coloured image. The reflection density was measured with a Shimadzu UV 365 spectrophotometer; FIG. 2a plots the result against wavelength. The corresponding "monomer" (compound I) is also shown showing that the chromophores in the product of the invention are those of the "monomer"; the invention entails no significant loss in colour forming capability per unit weight of colour former.

3. NMR Spectrum

This indicated the presence of a mixture of isomers corresponding to the structures of general formulae (IIIa) to (IIId) set out earlier.

In further tests the compound was encapsulated as follows:

2.32 g of the "tar state" compound, an unpurified yellow oil, was dissolved in 230.13 g of a 50° C. mixture of two parts by weight of a di-isopropylnaphthalene isomer blend and one part by weight kerosene.

The resulting 1% solution was then encapsulated by coacervation as known in the art and for example generally described in British Patent No. 870,476, the film-forming polymers used being gelatin, carboxymethyl cellulose (CMC), and vinylmethylether/maleic anhydride copolymer (PVMMA). The resulting micro-capsules were formulated into a microcapsule coating composition with a gelatinized starch binder and ground cellulose fibre floc as a "stilt material" for preventing accidental microcapsule rupture. The coating composition was applied to a conventional carbonless base paper by means of a laboratory Meyer bar coater at an approximate coat weight (when dry) of 6 gm$^{-2}$.

After drying, a sample of the resulting CB paper was placed in face to face contact with a conventional CF paper having an acid-washed montmorillonite clay as the main colour developing constituent. The CB-CF couplet so produced was passed through a laboratory calender so as to rupture the microcapsules and produce a coloured image on the CF paper.

Figure 2B:
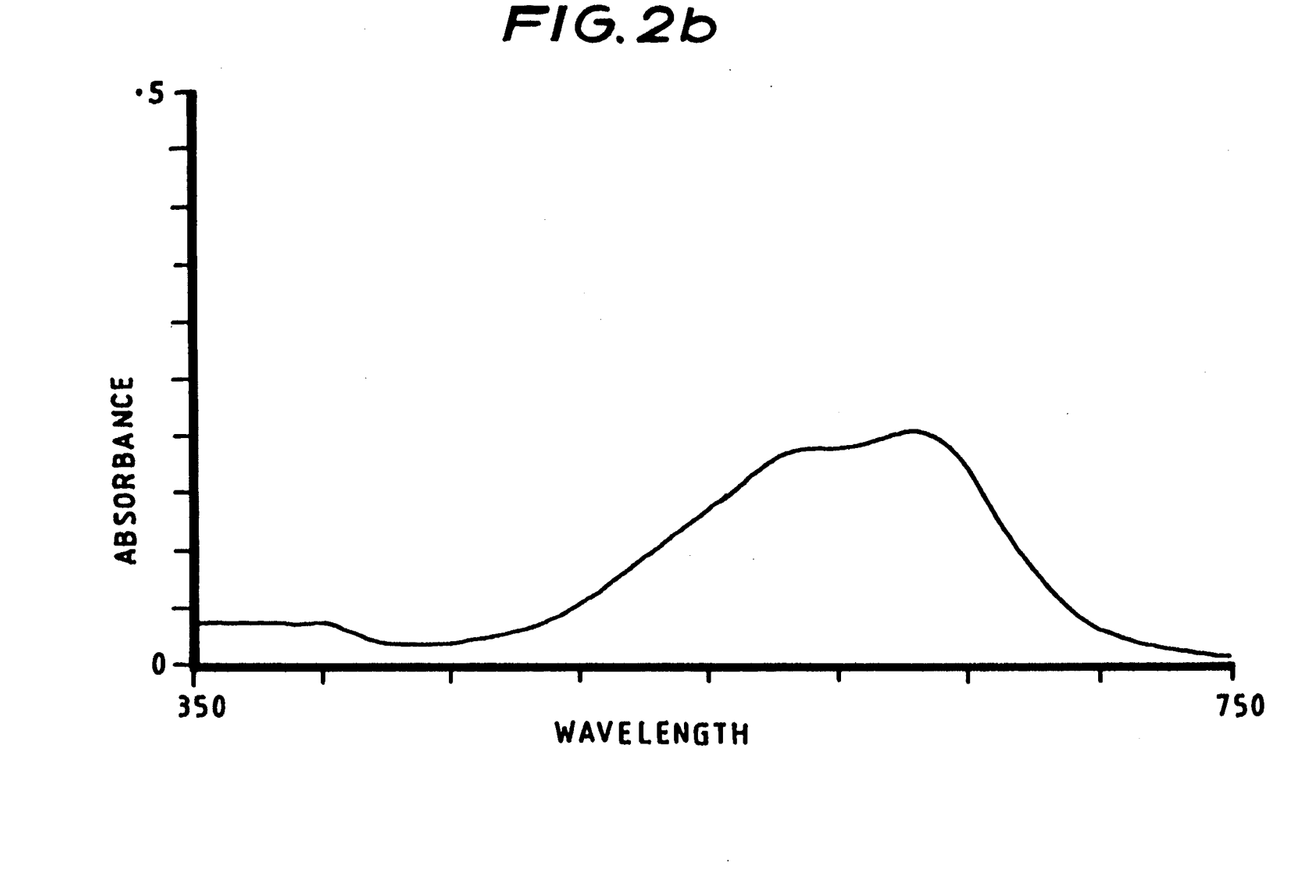
FIG. 2b reflectance density spectrum of the compound of Example 1, from a micro-capsule coating.

The reflectance spectrum of the coloured area was measured using a Philips PU 8800 L/V/visible spectrophotometer fitted with a PU/908/24 integrating spheroid. The spectrum obtained (FIG. 2b) corresponded to that obtained with compound XIV prior to encapsulation, so confirming that the compound can be encapsulated without difficulty, and that a good image is obtained at microcapsule coat weights of the same order as are used in commercial carbonless papers.

EXAMPLE 2 (TABLE 1, COMPOUND 3)

4,4'-Bis[3-(4-methoxyphenyl)-3-iso-propoxy-1-propenyl]-N-benzyldiphenyl amine (XV)

STAGE 1

4,4'-Bis[3-(4-methoxyphenyl)-3-oxo-1-propenyl]-N-benzyldiphenyl amine 4-methoxyacetophenone (10.0 g. 0.066 mol) and 4,4'-diformyl-N-benzyldiphenyl amine (10.3 g. 0.033 mol) were dissolved in ethanol (150 ml) in a 300 ml three-necked round bottom flask fitted with a mechanical stirrer and a dropping funnel. The third neck was stoppered and used to obtain samples for monitoring during the reaction. Aqueous sodium hydroxide solution (15 ml of 30 w/v%) was added dropwise to the vigorously stirred ethanolic solution at ambient temperature. A yellowish orange tar started separating from the reaction mixture immediately. Stirring was continued for about twenty hours and ethanol was removed on a rotary evaporator. The title compound was isolated by an extraction with toluene, washed successively with water and the solvent was removed. 16.5 g of the crude tar was purified with mixed solvent of acetone and ethanol to give 12.0 g (62.8% of theory) of 4,4'-Bis[3-(4-methoxyphenyl)-3-oxo-1-propenyl]-N-benzyldiphenylamine with a melting point of 128°~140° C.

STAGE 2

4,4'-Bis[3-(4-methoxyphenyl)-3-iso-propoxy-1-propenyl-N-benzyldiphenyl amine

4,4'-Bis[3-(4-methoxyphenyl)-3-oxo-1-propenyl]-N-benzyldiphenylamine (5.8 g. 0.01 mol) prepared in Stage 1 above and aluminium-iso-propoxide (8.2 g. 0.04 mol) were dispersed in 2-pentanol (150 ml). The temperature of reaction mixture was raised to 110° C. and the reaction was continued for two and a half hours distilling out 2-pentanol gradually. After the reaction was complete, toluene (100 ml) and hot water (300 ml) were added into reaction mixture. Toluene layer was separated and treated with active carbon. The solvent was removed to give 6.1 g (91.4% of theory) of 4,4'-Bis[3-(4-methoxyphenyl)-3-iso-propoxy-1-propenyl]-N-benzyldiphenyl amine as a pale yellow tar. The λ max solution spectrum value was 617 nm.

EXAMPLE 3 (TABLE 1, COMPOUND 2)

4,4'-Bis[3-(4-methoxyphenyl)-3-iso-propoxy-1-propenyl]-N-n-octyldiphenyl amine

EXAMPLE 4 (TABLE 1, COMPOUND 1)

4,4'-Bis[3-(4-methoxyphenyl)-3-iso-propoxy-1-propenyl]-N-n-butyldiphenyl amine

STAGE 1

4,4'-Bis[3-(4-methoxyphenyl)-3-oxo-1-propenyl]-N-n-octyldiphenyl amine

4-Methoxyacetophenone (15.0 g. 0.1 mol) and 4,4'-diformyl-N-n-octyldiphenyl amine (16.8 g. 0.05 mol) were dissolved in ethanol (200 ml) in a 300 ml three-necked round bottom flask fitted with a mechanical stirrer and a dropping funnel. The third neck was stoppered and used to obtain samples for monitoring during the reaction. Aqueous sodium hydroxide solution (20 ml of 30 w/v%) was added dropwise to the virorously stirred ethanolic solution at ambient temperature. A yellowish orange tar started separating from the reaction mixture immediately. Stirring was continued for about twenty hours and ethanol layer was removed. The title compound in residue was isolated by an extraction with toluene, washed successively with water and the solvent was removed. 30 g of the crude tar was purified with mixed solvent of acetone and ethanol to give 14.8 g (49.2% of theory) of 4,4'-Bis[3-(4-methoxyphenyl)-3-oxo-1-propenyl]-N-n-octyldiphenyl amine as an amorphous solid.

STAGE 2

4,4'-Bis[3-(4-methoxyphenyl)-3-iso-propoxy-1-propenyl]-N-n-octyldiphenyl amine 4,4'-Bis[3-(4-methoxyphenyl)-3-oxo-1-propenyl]-N-n-octyldiphenyl amine (6.0 g. 0.01 mol) prepared in Stage 1 above and aluminium-iso-propoxide [8.2 g. 0.04 mol) were dispersed in 2-propanol (160 ml). The temperature of reaction mixture was raised to 80° C. and the reaction was continued for two and a half hours distilling out 2-propanol gradually. After the reaction was complete, toluene (100 ml) and hot water (300 ml) were added into reaction mixture. Toluene layer was separated and treated with active carbon. The solvent was removed to give 6.5 g (94.2% of theory) of 4,4'-Bis[3-(4-methoxyphenyl)-3-iso-propoxy-1-propenyl]-N-octyldiphenyl amine as a pale yellow tar. The λ max solution spectrum value was 572 nm.

STAGE 1

4,4'-Bis[3-(4-methoxyphenyl)-3-oxo-1-propenyl]-N-n-butyldiphenyl amine

4-Methoxyacetophenone (15.0 g. 0.1 mol) and 4,4'-diformyl-N-n-butyldiphenyl amine (11.6 g. 0.04 mol) were dissolved in ethanol (200 ml) in a 300 ml three-necked round bottom flask fitted with a mechanical stirrer and a dropping funnel. The third neck was stoppered and used to obtain samples for monitoring during the reaction. Aqueous sodium hydroxide solution (20 ml of 30 w/v%) was added dropwise to the vigorously stirred ethanolic solution at ambient temperature. A yellowish orange solid started separating from the reaction mixture immediately. Stirring was continued for about twenty hours. The title compound was isolated by vacuum filtration, washed successively with ethanol and water and dried at 60° C. to give 19.1 g (87.6% of theory) of 4,4'-Bis[3-(4-methoxyphenyl)-3-oxo-1-propenyl]-N-n-butyldiphenyl amine with a melting point of 113°~127° C.

STAGE 2

4,4'-Bis[3-(4-methoxyphenyl)-3-iso-propoxy-1-propenyl]-N-n-butyldiphenyl amine

4,4'-Bis[3-(4-methoxyphenyl)-3-oxo-1-propenyl]-N-n-butyldiphenyl amine (5.45 g. 0.01 mol) prepared in Stage 1 above and aluminium-iso-propoxide (8.2 g. 0.04 mol) were dispersed in 2-propanol (150 ml). The temperature of reaction mixture was raised to 80° C. and the reaction was continued for four hours distilling out 2-propanol gradually. After the reaction was complete, toluene (100 ml) and hot water (300 ml) were added into reaction mixture. Toluene layer was separated and treated with active carbon. The solvent was removed to give 5.5 g (86.7% of theory) of 4,4'-Bis[3-(4-methoxyphenyl)-3-iso-propoxy-propenyl]-N-n-butyldiphenyl amine as a pale yellow tar. The λ max solution spectrum value was 575 nm.

EXAMPLE 5 (TABLE 1, COMPOUND 4)

4,4'-Bis[3-(4-butoxyphenyl)-3-iso-propoxy-1-propenyl]-N-methyldiphenyl amine

EXAMPLE 6 (TABLE 1, COMPOUND 6)

4,4'-Bis[3-(4-benzyloxyphenyl)-3-sec-pentyloxy-1-propenyl]-N-methyldiphenyl (XVIII)

(XIX)

STAGE 1

4,4'-Bis[3-(4-butoxyphenyl)-3-oxo-1-propenyl]-N-methyldiphenyl amine

4-Butoxyacetophenone (15.7 g. 0.06 mol) and 4,4'-diformyl-N-methyldiphenyl amine (5.9 g. 0.025 mol) were dissolved in ethanol (100 ml) in a 300 ml three-necked round bottom flask fitted with a mechanical stirrer and a dropping funnel. The third neck was stoppered and used to obtain samples for monitoring during the reaction. Aqueous sodium hydroxide solution (10 ml of 30 w/v%) was added dropwise to the vigorously stirred ethanolic solution at ambient temperature. A yellowish orange solid started separating from the reaction mixture immediately. Stirring was continued for about twenty hours. The title compound was isolated by vacuum filtration, washed successively with ethanol and water and dried at 60° C. to give 14.0 g (95.4% of theory) of 4,4'-Bis[3-(4-butoxyphenyl)-3-oxo-1-propenyl]-N-methyldiphenyl amine with a melting point of 160.3°~162.5° C.

STAGE 2

4,4'-Bis[3-(4-butoxyphenyl)-3-iso-propoxy-1-propenyl]-N-methyldiphenyl amine

4,4'-Bis[3-(4-butoxyphenyl)-3-oxo-1-propenyl]-N-methyldiphenyl amine (5.87 g. 0.01 mol) prepared in Stage 1 above and aluminium-iso-propoxide (8.2 g. 0.04 mol) were dispersed in 2-propanol (100 ml). The temperature of reaction mixture was raised to 80° C. and the reaction was continued for six hours distilling out 2-propanol gradually. After the reaction was complete, toluene (100 ml) and hot water (300 ml) were added into reaction mixture. Toluene layer was separated and treated with active carbon. The solvent was removed to give 5.5 g (81.4% of theory) of 4,4'-Bis[3-(4-butoxyphenyl)-3-iso-propoxy- 1-propenyl]-N-methyldiphenyl amine as a pale yellow tar. The $\lambda$ max solution spectrum value was 574 nm.

STAGE 1: 4,4'-Bis[3-(4-benzyloxyphenyl)-3-oxo-1-propenyl]-N-methyldiphenyl amine 4-Benzyloxyacetophenone (13.6 g. 0.06 mol) and 4,4'-diformyl-N-methyldiphenyl amine (5.9 g. 0.025 mol) were dissolved in ethanol (100 ml) in a 300 ml three-necked round bottom flask fitted with a mechanical stirrer and a dropping funnel. The third neck was stoppered and used to obtain samples for monitoring during the reaction. Aqueous sodium hydroxide solution (10 ml of 30 w/v%) was added dropwise to the vigorously stirred ethanolic solution at ambient temperature. A yellowish orange solid started separating from the reaction mixture immediately. Stirring was continued for about twenty hours. The title compound was isolated by vacuum filtration, washed successively with ethanol and water and dried at 60° C. to give 14.0 g (95.4% of theory of 4,4'-Bis[3-(4-benzyloxyphenyl)-3-oxo-1-propenyl]-N-methyldiphenyl amine with a melting point of 185°~200° C.

STAGE 2: 4,4'-Bis[3-(4-benzyloxyphenyl)-3-sec.-pentyloxy-1-propenyl]-N-methyldiphenyl amine 4,4'-Bis[3-(4-benzyloxyphenyl)-3-oxo-1-propenyl]-N-methyldiphenyl amine (6.5 g. 0.01 mol) prepared in Stage 1 above and aluminium sec.-pentyloxide (8.2 g. 0.04 mol) were dispersed in 2-pentanol (160 ml). The temperature of reaction mixture was raised to 115° C. and the reaction was continued for two hours distilling out 2-propanol gradually. After the reaction was complete, toluene (100 ml) and hot water (300 ml) were added into reaction mixture. Toluene layer was separated and treated with active carbon. The solvent was removed to give 6.7 g (90.1% of theory) of 4,4'-Bis[3-(4-benzyloxyphenyl)-3-sec-pentanoxy-propenyl]-N-methyldiphenyl amine as a pale yellow tar. The $\lambda$ max solution spectrum value was 576 nm. The product has only low crystallisation tendency in view of the presence of isomers as below, which were identified by NMR spectroscopy and which can be separated if desired The structures, with the title compound first are:

trans-a,a-form (compare III a)

XX trans-a,b-form (compare III c and III d, here the same as $R^2 = R^3 = H$, $R^6 = R^7 = $ sec.-pentyl, etc)

XXI trans-b,b-form (compare III b)

XXII

We believe that most if not all of the other compounds synthesized by the MPV route also contain a mixture of isomers of the kind just referred to, but except for Example 1 this has not been confirmed by running NMR spectra.

EXAMPLE 7 (TABLE 1, COMPOUND 23)

XXIII 4,4'-Bis[3-(4-methoxyphenyl)-3-oxo-1-propenyl]-N-methyl-diphenylamine (2.65 g 0.005 mol) was dissolved in toluene (100 cc) in a 300 ml 3-necked round bottom flask fitted with a mechanical stirrer, a water cooled condenser and a thermometer. Methanol (100 ml) was added to the solution and the temperature was raised to 50° C. Sodium borohydride (6.0 g) was then added gradually at 50° C. for about 2 hours. After completion of the addition of sodium borohydride the reaction mixture was kept stirred for 1 hour at 50° C. After the reaction was complete, the reaction mixture was poured into water (500 ml). Toluene Layer was separated and evaporated, 2.5 g of 4,4'-Bis[3-(4-methoxyphenyl)-3-hydroxy-1-propenyl]-N-methyldiphenyl amine being obtained as an oily product.

EXAMPLE 8 (TABLE 1, COMPOUND 27)

XXIV 4,4'-Bis[3-phenyl-3-oxo-1-propenyl]-N-n-octyldiphenylamine (the chalcone corresponding to compound 19) (2.0 g 0.0037 mol) was dissolved in toluene (90 cc) in a 4-necked round bottom flask fitted with a stirrer, a thermometer, a dropping funnel and a water cooled condenser itself fitted with a guard tube containing calcium chloride to prevent the ingress of moisture. And dried ether (50 cc) was added in the toluene solution.

Phenyl lithium (7.4 ml of a 2M solution in cyclohexanediethyl ether) was added using a dropping funnel at ambient temperature.

After completion of the addition of phenyl lithium the reacton mixture was kept stirred for 6 hours at 40° C.

When the reaction was complete, the reaction mixture was poured into cooled water (200 cc) gradually. After stirring for 1 hour the toluene layer was separated and treated with active carbon. The toluene was removed using a rotary evaporator to give 2.4 g (93.5% of theory) of 4,4'-Bis[3,3-diphenyl-3-hydroxy-1-propenyl]-N-n-octyldiphenylamine as a pale yellow tar.

We claim:

1. A compound of the structure:

or a structural isomer thereof wherein one or both ethylenic links are adjacent to a terminal rather than central aryl group, or corresponding chalcones thereof; where in formula (IIIa) $A_1$ and $A_2$, may be the same or different, and each represents a hydrogen or aryl group, $R^1$ represents hydrogen or an alkyl or aralkyl group, $R^2$ and $R^3$, may be the same or different, and each represent hydrogen, a halogen, or an alkyl, alkoxy, aralkoxy, primary amino, secondary amino or N-heterocyclic group, $R^4$ and $R^5$, may be the same or different, and each represents hydrogen, a halogen or an alkyl, alkoxy or aralkoxy group, and $R^6$ and $R^7$, may be the same or different, and each represents hydrogen or an alkyl, aryl or aralkyl group.

2. A compound of formula (IIIa) according to claim 1, or structural isomer or chalcone thereof, wherein $R^1$ is a $C_1$-$C_8$ alkyl group or benzyl group.

3. A compound of formula (IIIa) according to claim 1, or structural isomer or chalcone thereof, wherein at least one of $R^1$, $R^2$, $R^3$, $R^4$ and $R^5$ represents a chloro, bromo, $C_1$-$C_8$ alkyl, $C_1$-$C_8$ alkoxy or benzyloxy group.

4. A compound of formula (IIIa) according to claim 1, or structural isomer or chalcone thereof, wherein at least one of $R^2$ and $R^3$ represents a di($C_1$-$C_8$)alkylamino, dibenzylamino, piperidino, pyrrolidino or morpholino group.

5. A compound of formula (IIIa) according to claim 1, or structural isomer or chalcone thereof, wherein at least one of $R^2$ and $R^3$ represents a dimethylamino group.

6. A compound of formula (IIIa) according to claim 1, or structural isomer or chalcone thereof, wherein at least one of $R^6$ and $R^7$ represents a $C_1$-$C_8$ alkyl, phenyl or benzyl group.

7. A compound of formula (IIIa) according to claim 1, or structural isomer or chalcone thereof, wherein $R^1$ is a methyl, n-butyl, n-octyl or benzyl group, $R^2$ and $R^3$, may be the same or different, and each represents hydrogen, or a methyl, bromo, methoxy, n-butyl, n-octyloxy, benzyloxy, dimethylamino, dibenzylamino, piperidino, pyrrolidino or morpholino group, $R^4$ and $R^5$, may be the same or different, and each represents hydrogen or a chloro, methyl, methoxy, n-butoxy, n-octyloxy or benzyloxy group, and $R^6$ and $R^7$, may be the same or different, and each represents hydrogen or a methyl, ethyl or isopropyl group.

8. A compound of formula (IIIa) according to claim 1, wherein $A_1$ and $A_2$ are both hydrogen, $R^1$ is a methyl group, $R^2$ and $R^3$ are both $CH_3$—O—, $R^4$ and $R^5$ are both hydrogen and $R^6$ and $R^7$ are both isopropyl groups.

9. A compound of formula ABA wherein the A groups are identical, selected from the group consisting of compounds (i)-(xxvii), wherein:

(i)

(ii)

(iii)

(iv)

(v) (A)

(B)

(vi)

(A)

(vii)

(B)

(viii)

(A)

(ix)

(B)

(x) (A)

(A)  (B)

(xi)

(A)

(B)

(xii)

(A)

(B)

(xiii)

(A)

(B)

(xiv)

(A)

(B)

(xv)

(A)

(B)

(xvi)

(A)

(B)

(xvii)

(A)

(B)

(xviii)

(A)

(B)

(xix)

(A)

(B)

(xx)

(A)

(B)

(xxi)

(A)

(B)

(xxii)

(A)

(B)

(xxiii)

(A)

(B)

(xxiv)

(A)

(B)

(xx)

(A)

(B)

(xxvi)

(A)

(B)

-continued (xxvii)

-continued (A)

(B)

10. Pressure or heat sensitive record material comprising a compound of the structure set out in claim 1 as a chromogenic compound.

* * * * *